United States Patent
Doughty (10) Patent No.: US 7,605,389 B1
(45) Date of Patent: Oct. 20, 2009

(54) PARTICLE DETECTOR WITH PARTICLE TRAPPING DEVICE

(75) Inventor: Chris Doughty, North Andover, MA (US)

(73) Assignee: Verionix, Inc., North Andover, MA (US)

( * ) Notice: Subject to any disclaimer, the term of this patent is extended or adjusted under 35 U.S.C. 154(b) by 312 days.

(21) Appl. No.: 11/761,357

(22) Filed: Jun. 11, 2007

Related U.S. Application Data (60) Provisional application No. 60/804,463, filed on Jun. 12, 2006.

(51) Int. Cl.
*H01J 49/00* (2006.01)
*H01J 49/02* (2006.01)
*H01J 49/04* (2006.01)
*H01J 49/10* (2006.01)
*G01N 15/02* (2006.01)

(52) U.S. Cl. .................. 250/574; 250/576; 250/288; 356/336; 73/865.5; 324/71.4

(58) Field of Classification Search ................ 250/281, 250/282, 283, 288, 292, 423 R, 424, 489, 250/573, 574, 576, 222.1, 222.2; 356/335–343; 73/865.5; 324/71.4
See application file for complete search history.

(56) References Cited

U.S. PATENT DOCUMENTS

| 5,464,975 | A | * | 11/1995 | Kirchner et al. ............. 250/283 |
| 5,641,919 | A | * | 6/1997 | Dahneke ..................... 73/865.5 |
| 5,835,211 | A | * | 11/1998 | Wells et al. ................. 356/336 |
| 6,553,849 | B1 | * | 4/2003 | Scofield et al. ............ 73/865.5 |
| 7,119,331 | B2 | * | 10/2006 | Chang et al. ................ 250/292 |
| 7,123,361 | B1 | * | 10/2006 | Doughty ..................... 356/316 |
| 7,309,842 | B1 | * | 12/2007 | Doughty ................ 219/121.43 |
| 2005/0029448 | A1 | * | 2/2005 | Chang et al. ................ 250/292 |
| 2006/0043282 | A1 | * | 3/2006 | Hidalgo et al. ............. 250/287 |
| 2008/0156984 | A1 | * | 7/2008 | Makarov et al. ........... 250/288 |

* cited by examiner

*Primary Examiner*—John R Lee
(74) *Attorney, Agent, or Firm*—Kurt Rauschenbach; Rauschenbach Patent Law Group, LLC

(57) ABSTRACT

A particle detector includes an input port for receiving gas and particulate matter. A charging source generating positively and negatively charged species that charges at least some particulate matter in charging region, thereby generating a plurality of charged particles. A trapping region is formed having a potential energy minimum that attracts and confines the plurality of charged particles. A detector detects charged particles in the trapping region.

33 Claims, 6 Drawing Sheets

| Actual number of particles | Line Fraction Probed | Particles Detected (single pass) | 3 SIGMA Statistical Variance | Relative Variance |
|---|---|---|---|---|
| 1000 | 1% | 10 | 9.49 | 95% |
| 1000 | 10% | 100 | 30.00 | 30% |
| 1000 | 50% | 500 | 67.08 | 13% |
| 1000 | 95% | 950 | 92.47 | 10% |

PARTICLE DETECTOR WITH PARTICLE TRAPPING DEVICE

RELATED APPLICATION SECTION

This application claims priority to U.S. Provisional Patent Application Ser. No. 60/804,463, filed Jun. 12, 2006, entitled "Trapping Particle Device", the entire application of which is incorporated herein by reference.

The section headings used herein are for organizational purposes only and should not to be construed as limiting the subject matter described in the present application.

BACKGROUND SECTION

This invention relates generally to particle detectors. A particle is defined herein as any agglomeration of matter. Particles can include, for example, atomic species, molecular species, viruses, biological cells, and nanotubes. There are numerous types of particle detectors known in the art. One type of charged particle detector is an optical detector that uses a light beam, such as a laser, to scatter light from the particles, thereby generating a photocurrent at a detector. The resulting photocurrent waveforms are then analyzed to obtain the particle size information. The scattering cross section of particles is a function of the wavelength of the analyzing light beam. Particle detectors using light beams generally can only detect particles that are over about 100 nm because of wavelength limitations. See, for example, U.S. Pat. Nos. 5,835,211 and 6,784,990 for a description of particle detection based on laser scattering and laser light extinction.

Another type of particle detector is a condensation particle detector. Condensation particle detectors can be used to detect particles with dimensions below 100 nm. Particles this small act as nucleation sites for condensation of liquid droplets. The liquid droplets are of a sufficient size that can be easily detected with a light beam or other detection means. However, condensation particle detectors do not provide any information on the particle size.

Another type of particle detector is a time-of-flight particle detector. Time-of-flight particle detectors measure particles arriving at the detector as a function of time. The mass of a particle can be determined by measuring the time it takes a particle to be detected after passing through a known electric field. See for example, U.S. Pat. No. 6,553,849 for a description of time-of-flight (TOF) particle detector.

BRIEF DESCRIPTION OF THE DRAWINGS

The aspects of this invention may be better understood by referring to the following description in conjunction with the accompanying drawings. Identical or similar elements in these figures may be designated by the same reference numerals. Detailed description about these similar elements may not be repeated. The drawings are not necessarily to scale. The skilled artisan will understand that the drawings, described below, are for illustration purposes only. The drawings are not intended to limit the scope of the present teachings in any way.

DETAILED DESCRIPTION

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

It should be understood that the individual steps of the methods of the present invention may be performed in any order and/or simultaneously as long as the invention remains operable. Furthermore, it should be understood that the apparatus and methods of the present invention can include any number or all of the described embodiments as long as the invention remains operable.

While the present teachings are described in conjunction with various embodiments and examples, it is not intended that the present teachings be limited to such embodiments. On the contrary, the present teachings encompass various alternatives, modifications and equivalents, as will be appreciated by those of skill in the art.

There are many applications for particle detectors. For example, particle detectors are commonly used to monitor manufacturing environments. Most semiconductor devices are fabricated in clean rooms or in processing tools that precisely limit the number of particles over a certain size per cubic foot. Particles can cause defects in the semiconductor material structures that can degrade the performance or the lifetime of the semiconductor device and can even render the semiconductor device inoperable.

The particle size is carefully monitored and controlled in some biological, medical, and health care environments. Many pathogens (i.e. viruses, bacteria and spores) have particles sizes that are in the range of 100-10,000 nm. It is highly desirable to be able to detect such particles and hold them and/or deliver them to another system.

In many industries, such as the nanotechnology, chemical, pharmaceutical, petrochemical, and semiconductor industries, small particles form the basis of a manufactured product, either as a final product or as a constituent of the product. In particular, the nanotechnology industry is rapidly growing. Workers in the nanotechnology industry are routinely exposed to small particles. It is, therefore, important to monitor and control the size of the particles for many processes in these industries.

Work environments where small particles are generated may be a health hazard and, therefore, must be carefully monitored. In particular, particles having diameters that are in the range of 50 nm are thought to be harmful to humans. Currently there are no inexpensive detection methods for such small particles.

In addition, there are applications where particulate matter must be analyzed for certain physical, chemical, or biological traits. Particulate mater is defined herein as any agglomeration that is in the size range of a few nanometers to about 10 um. These applications sometimes require characterizing, sorting, and/or confining small particles for interrogation by other physical, chemical, or biological traits. Currently there are no inexpensive methods of detection or such small particles.

Figure 1:
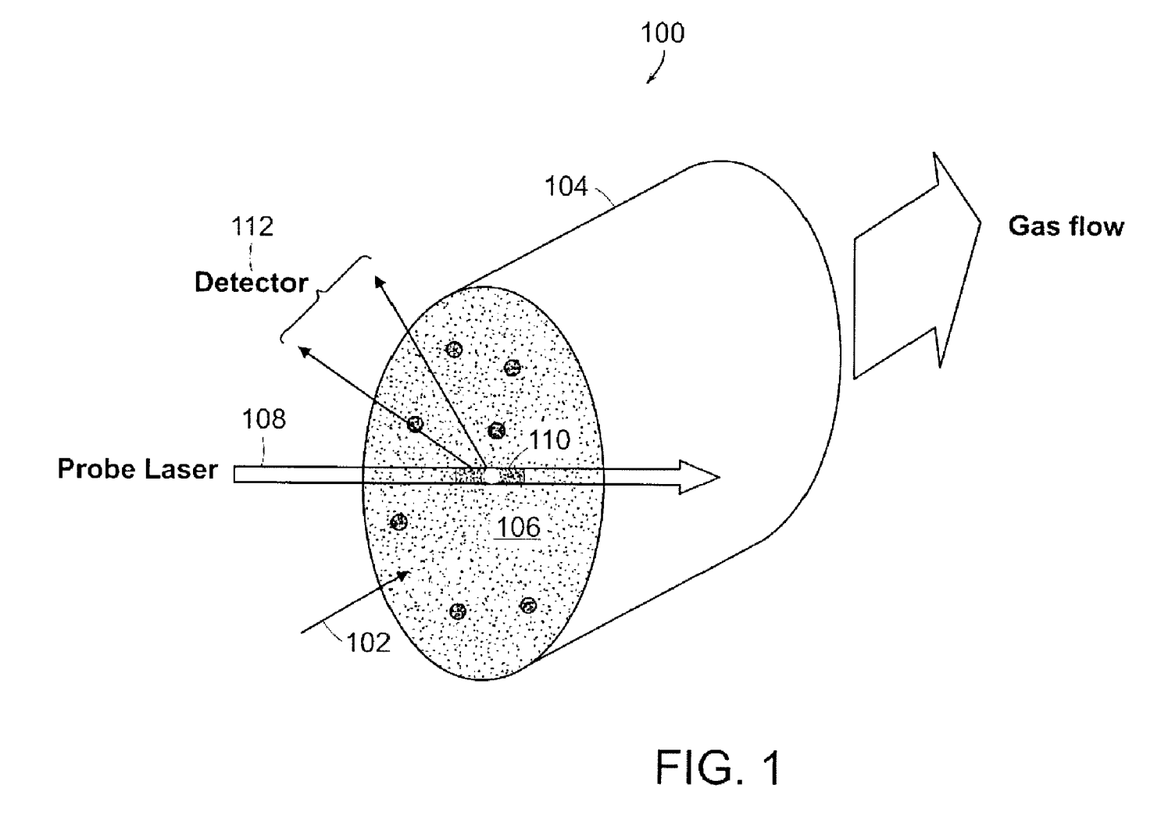
FIG. 1 illustrates a cross sectional diagram of a known laser particle detector.

FIG. 1 illustrates a cross sectional diagram of a known laser particle detector 100. A gas containing particles subject to measurement flows through an entrance or input port 102 of a chamber or tube 104 and forms a gaseous medium 106 containing particles in the tube 104. A laser beam 108 is directed to a region 110 in the tube 104. The laser beam 108 probes or interrogates the gaseous medium 106 present in the region 110. The cross sectional diagram of the laser particle detector 100 indicates that there is a relatively small probe volume in such laser particle detectors.

Particles that have been interrogated by the laser beam 108 scatter photons to a photon detector 112. A number and size of particle passing through the laser beam 108 can be related to the number of counts registered by the detector 112. The narrow beam width of the laser beam 108 and the detector optics used to direct the photons to the detector 112 only allows photons from the relatively small region 110 of the tube 104 to reach the detector 112. Particles which do not pass through the laser beam 108 will not be detected. Consequently, most of the particles in the gaseous medium are not detected.

One feature of the particle detector of the present invention is that it has the ability to collect particles from a system over a large area and confine them for detection within a much smaller volume. This feature allows very low density particle environments, such as clean rooms and semiconductor manufacturing equipment, to be analyzed for particle counts, particle densities and population with substantially enhanced statistical relevance.

Figure 2:
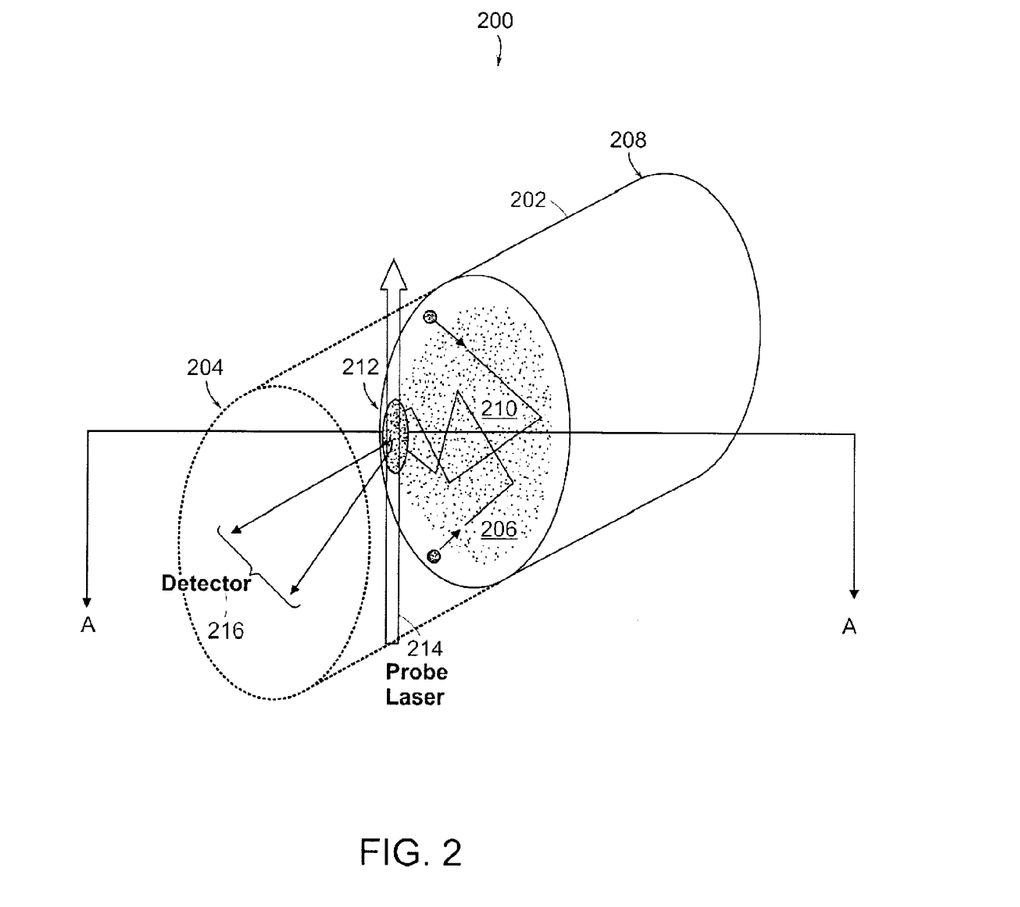
FIG. 2 illustrates a cross sectional diagram of a particle detector according to the present invention.

FIG. 2 illustrates a cross sectional diagram of a particle detector 200 according to the present invention. A chamber, conduit, or tube 202 is used to contain a gas comprising particles subject to measurements. FIG. 2 shows a circular tube. However, it should be understood that any type and shape of enclosure can be used to contain the gas. Also, it should be understood that, in some embodiments, the gas is not contained. The gas containing the particles subject to measurement flows through an entrance or input port 204 of the tube 202 and forms a gaseous medium 206 containing particles in the tube 202. Alternatively, the gas containing the particles subject to measurement diffuses through the tube 202. The gas exits the tube 202 through an exit or output port 208.

The particle detector 200 includes an ionization or charging source, such as a microplasma source, that generates charged species in a charging region 210. The charging region 210 is a volume in space where particles may be charged by attachment of electrons or ions, and where a gradient in potential energy acts to transport charged particles. The charging region 210 is established in a geometry that may be as large as the total cross section of the tube 202. These charged species include electrons, atomic and molecular ions, and charged particles. For example, in some embodiments, a plasma discharge is used to generate the charged species as described herein.

The particle detector 200 also includes a means for generating a trapping region 212. The trapping region 212 is a region having a relatively low potential energy for the charged particles that traps the charged particles. Regions having relatively low potential energy are sometimes referred to as potential wells. There are several ways of forming the trapping region 212 according to the present invention. In one embodiment, the trapping region 212 is formed by creating a potential well for charged species in a localized region.

In one embodiment, a plasma is generated having a shape that creates the trapping region 212. Plasmas contain electrons and ions that have opposite charge and greatly varying mobilities. The entire plasma is charge neutral. In order to maintain charge neutrality, a sheath potential is formed relative to the grounded and floating surfaces adjacent to the plasma. The sheath potential acts to retard the flow of electrons and to enhance the flow of positive ions across the sheath so that the total charge of the plasma is neutral. Therefore, the plasma sheath forms a low potential region in the plasma that is referred to herein as a potential well. Consequently, negatively charged macroscopic species, such as negatively charged particles, are trapped in the potential well.

For example, in one embodiment, the plasma is established so that forces, such as gravitational forces, ion drag forces from collisions with ions, and viscous drag forces from neutral atoms and molecules flowing in a preferred direction cause the total potential for particles to reach a minimum in a trapping region. For example, a charging region can generate a flat, non-localized particle potential minimum between two widely separated endpoints, when subjected to parallel ion or viscous drag forces that produce a linearly varying potential between the two endpoints. In such a plasma, the trapping region can be dumped by removal of the plasma driving force or by a mechanical reconfiguration, such as a rotation of the plasma potential axis so that it becomes orthogonal to the viscous or ion drag or gravitational forces.

In particular, a microplasma can be used to generate localized trapping regions that have areas which are much smaller than the area of the charging region 210. Some microplasma sources inductively couple electric and magnetic fields with a high efficiency resonant antenna structure. See, for example, Hopwood, J. Vac. Sci. Technol. B, 18.5, September/October 2000, pg. 2446. Suitable microplasma sources are described in U.S. Pat. No. 7,123,361, entitled "Microplasma Emission Spectrometer" and U.S. patent publication Ser. No. 10/907,024, entitled "Shielded Microplasma Source," which are incorporated herein by reference. Spectroscopic instruments that use microplasmas have been fabricated in which the microplasma dimensions are on order of a few millimeters and the sheath-to-volume ratio is in the range of 0.1 or larger for the plasma source region. Hence, the trapping region in these sources has dimensions that are in the range of a few millimeters with a volume is in the range of a few cubic millimeters.

Microplasmas create a localized source of electrons and ions which flow from a high density region into a lower density region. This flow creates a plasma sheath. Internal potentials in the plasma act to reduce the electron flow and to increase flow of positive ions from the source region. A trapping region forms with a potential well that attracts and then confines negatively charged species. The potential well in the trapping region can be extinguished by removing the driving force of the microplasma. For example, the microplasma can be driven by an antenna. When power to the antenna is terminated, the potential well in the trapping region will be extinguished. The charged particles will then exit the trapping region because of random motion and repulsive forces.

The trapping region 212 can also be generated using larger plasmas (non-microplasmas). For example, in one embodiment, a hollow cathode structure is used to generate a potential well within the plasma. Hollow-cathode structures include features, such as holes, trenches, and ridges, which are known to create localized regions of relatively high particle density plasmas. The hollow cathode structures can be symmetrical or asymmetrical. The hollow cathode structures can be formed from the driving electrode that generates the plasma. Such hollow cathodes are well known in the art. The density of electrons in the hollow cathode is relatively high, which establishes a potential difference from the tip of the hollow cathode to the plasma. In some embodiments, both microplasmas and hollow cathode structures are used to generate a potential well within the plasma.

For example, the hollow cathode can be a rectangular electrode with a high aspect ratio structure. A localized neck (smaller width region) or bump (larger width region) in the rectangular electrode can be used to locally modify the plasma density, electron flux and local particle potential energy so as to generate a potential well within the plasma. The trapping region can be emptied or dumped by removing or changing the power level of the driving power supply, or by physically changing the structure through moving components, flexing or bending to remove the hollow cathode structure.

The trapping region 212 can also be formed by generating an electric field by biasing at least one electrode or surface. The plasma will reach an equilibrium in which charge generation, recombination, and loss are balanced across the entire plasma boundary. By controlling the bias point of the at least one electrode or surface, internal potentials can be induced from the at least one electrode or surface to the plasma and within the plasma to the opposing surfaces. For example, a small surface can be biased relative to a much larger grounded area so as to attract electrons to the small surface to create an internal potential minimum for electrons, driving current flow. The resulting trapping region can be dumped by reversing or modifying the applied potentials or by removal of the driving source of the plasma. It should be understood that two or more methods of generating a trapping region can be used with the particle detector of the present invention.

In operation, particles enter into the input port 204 of the particle detector 200. The particles may originate from various sources, such as chemical, physical, biological sources. When the particles encounter the charged species, such as electrons and ions, in the charging region 210, either through random motion or by being transported along with the gas stream, the charged species transfers charge to the particles by well known charge attachment and transfer processes. The resulting charged particles are agglomerations of matter with dimensions that are in the range of a few nanometers to a few millimeters. The charged particles may or may not be spherical. In various embodiments, the charged particles can be metallic, insulating, or semiconducting.

The particle detector 200 is electrically biased so that charged species of one polarity (typically electrons) are repelled from the surface of the tube 202. The bias may be externally applied or may result from a self bias that is established by the potential difference between the inner surface of the tube 202 and the charged species. For example, in one embodiment, the outer surface of the tube 202 is electrically connected to ground potential. The plasma potential is then biased relative to the ground potential on the surface of the tube 202.

Once the particles are charged, the particles are subject to the electrodynamic potential that is established in the charging region 210 and to gravitational and drag forces. Each of the charged particles will have a mobility that can be expressed as $J=\mu^* pE$, where $\mu$ is the mobility, p is the density, and E is the electric field experienced by the particle. The mobility of the charged particles will depend on the scattering cross section of the species, the mass of the species, and the charge state of the species. The mobility will differ by many orders of magnitude for particles and for atomic and molecular ions and electrons.

The trapping region 212 is established within the charging region 210. The cross sectional line A-A through the trap region 212 is shown in FIG. 2. For particles at low temperatures (i.e. low mean kinetic energy) that are subject to a potential of several eV for a single charge at a potential of several Volts), the particles will be effectively trapped by the potential. The particle trapping is both spatial and temporal in nature as the particles are trapped in the spatial region where the potential is low and once entering this region will be unlikely to gain sufficient energy through random processes to escape. The enhancement in local particle density in the trapping region 212 is equal to the ratio of the charging volume at the entrance area to the volume of the trap region 212. Over time, the enhancement in local particle density increases further as all particles entering the trapping region 212 are localized in the trap region 212 volume, but only rarely exit.

After the particles are confined in the trapping region 212, the confined particles can be counted and/or analyzed by many different techniques. Because the particles are localized in the trapping region 212, which is inside the tube 202 rather than on the surface, it is much easier to count and/or analyze the particles compared with prior art particle detectors. For example, the particles can be counted by optical interrogation means and can be analyzed by fluorescence, emission spectrometry, absorption, and/or x-ray analysis. The analysis techniques can include light scattering detection, electrical detection, or extraction to a collection system for particle counting or for off-line chemical analysis by any number of the many techniques known in the art for analyzing particles, chemicals, molecules, cells viruses, or biological material.

The term "light scattering detection" as defined herein is a detection means where light is scattered from a particle or where light illuminates a particle causing some photo effect, such as fluorescence. Thus, light scattering detection includes detection of scattered photons and detection of fluorescence photons. Light scattering detection also includes detection of light extinction, which is the drop in the intensity of the optical signal due to particles in the beam. Also, light scattering detection includes interrogation of the particles by means of optical absorption or reemission of photon energy. The term "electrical detection" as defined herein is a detection means where particles are detected by their charge and/or their mass-to-charge ratio. Electrical detection includes direct detection of the charge delivered to a collection electrode, for example in time-of-flight detector, or in the detection of impedance effects due to the mass and charge of the particles and their response to varying EM fields.

In one embodiment, an optical interrogation means is used to measure the number of particles in the trapping region 212. For example, light scattering can be used to measure the number of particles in the trapping region 212 with a laser or light beam 214. The charged particles have a much higher scattering cross sections than atomic or molecular ions and/or electrons. The beam width of a laser beam or light beam 214 can be chosen to be approximately equal to the cross sectional area of the trapping region 212. The laser beam 214 can analyze a continuous stream of particles or can repeatedly analyze the same particles.

A detector analyzes the particles by measuring the light scattered by the particle with a photodetector 216. The photodetector 216 is positioned to receive photons emitted from the trap region 212. The count rate of photons detected by the photodetector 216 can be equated to a number and a size of particle passing through the light beam 214. The particle detection probability using light interrogation will increase by the ratio of the total cross sectional area of the tube 202 to the cross sectional area of the trap region 212 assuming a constant photodetector area. Extraneous light signals, such as from plasma emission or background light, can be removed by proper filtering, including wavelength and temporal filtering techniques known in the art.

Such a particle detector using light interrogation means is advantageous for many reasons. A high fraction of the particles can be detected. Also, a smaller photodetector area can be used to detect the photons generated in the trap region 212. Relatively small photodetectors will have lower dark current noise due to their smaller active area.

Particle analysis can be performed in the trapping region 212 and/or after extraction through the output port 208. In some embodiments, the output port 208 of the particle detector 200 is coupled directly to a particle analysis system. Also, in some embodiments, the output port 208 of the particle detector 200 is coupled to a filter or mechanical trap structure that confines the particles for analysis. For some measurements, the contents of a mechanical trap are analyzed after detection. For other measurements, the contents of a mechanical trap are discarded because they might contain hazardous materials or other waste which is desirable to separate from the main gas stream. In some measurement systems, it is desirable to include a trapping system on the pumping line upstream of the pump. Such a trapping system can ensure that little or no particulate matter reaches the pump, which enhances the pump lifetime in addition to allowing analysis of the particulate matter.

Figure 3A:
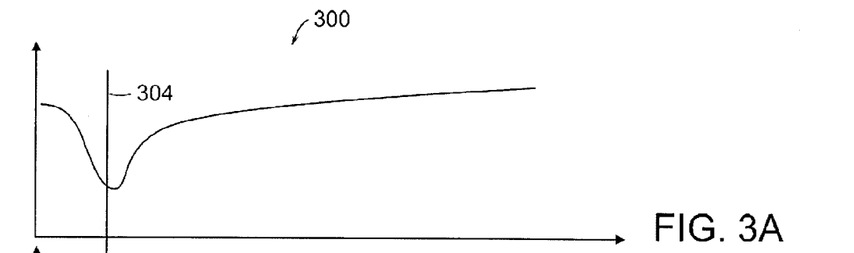
FIG. 3A presents a voltage potential diagram that illustrates the voltage potential in the tube shown in FIG. 2 as a function of distance along the cross sectional line A-A shown in FIG. 2.

FIG. 3A presents a voltage potential diagram 300 that illustrates the voltage potential in the tube 202 shown in FIG. 2 as a function of distance along the cross sectional line A-A shown in FIG. 2. Particles which enter the ionized region with a negative charge or which, during their time in the ionized region acquire a charge by ionization or by charge attachment will distribute according to their energy.

The voltage potential diagram 300 illustrates that particles entering the input port 204 of the tube 202 into the charging region 206 have a high probability of becoming charged, which is well known in the art. Particles entering into the charging region 210 with a negative charge or acquire a charge by ionization or by charge attachment will distribute in the trap region according to their energy. The voltage potential diagram 300 illustrates that once the particles are charged, they are attracted to the trap region 212. The particles entering in the trapping region 212 tend to have relatively low energy and high mobility.

Once the particles are in the trap region 212, they are held in the trap region 212 until the trap potential is changed or until the energy of the particles changes enough for the particles to overcome the potential in the trapping region 212. Over time, other particles will enter and be trapped in the trap region 212. The volume of the trap region 212 is relatively small compared with the volume of the charging region 210. The photodetector 216 location is indicated by a line 304 in voltage potential diagram 300. In many embodiments it is desirable to position the entrance of the photodetector 216 so that it receives substantially all of the photons generated in trapping region 212.

Figure 3B:
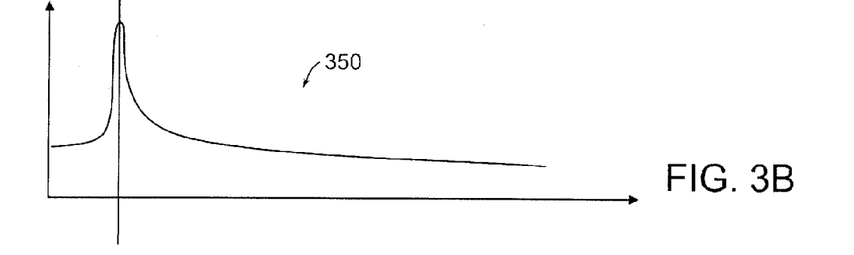
FIG. 3B presents a graph of particle density as a function of distance along the cross sectional line A-A shown in FIG. 2.

FIG. 3B presents a graph 350 of particle density as a function of distance along the cross sectional line A-A shown in FIG. 2. Particles are confined in the low-potential region with a spatial extent, which is determined by their energy and mobility according to conventional thermodynamic principles and distributions. In addition, the graph 350 shows that there is a peak density of particles in the trapping region 212 as expected. High energy particles would have a more widely spread distribution than lower energy particles, which are more effectively localized.

Figure 4:
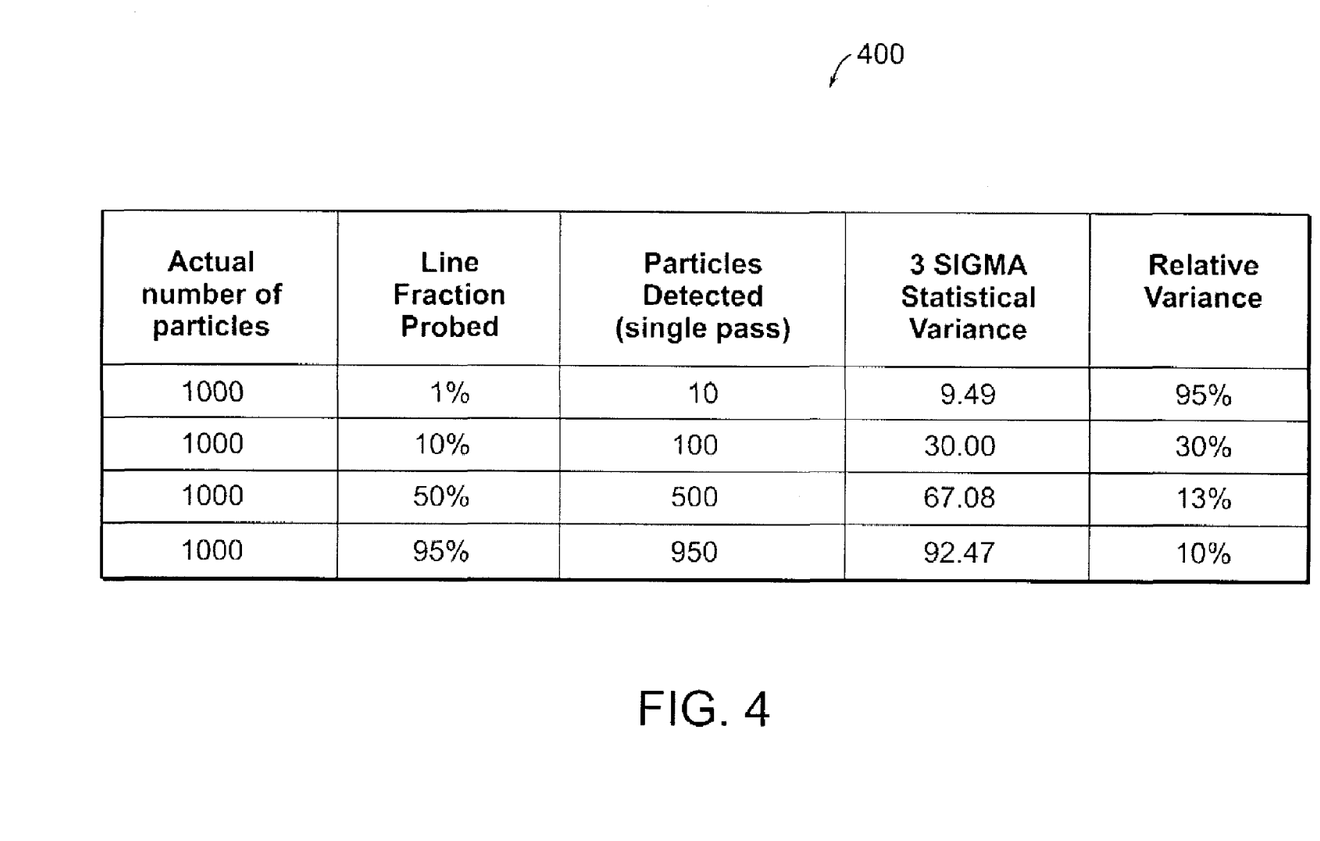
FIG. 4 illustrates a table of data illustrating the performance advantage of using a particle detector that includes a trapping region according to the present.

FIG. 4 illustrates a table 400 of data illustrating the performance advantage of using a particle detector that includes a trapping region according to the present invention. Data is presented for an actual number of particles that is equal to one thousand entering the input port in a unit time. Such an actual number of particles is typical for a time period of several minutes for detecting environments with a relatively low density of particles flowing past the detector, such as environments that are commonly seen in the semiconductor industry. The number of particles detected in a single pass and the associated statistical variance and relative variance is presented for different line fractions probed. The term "line fraction probed" is the fraction of the detection region that is probed by the laser to obtain detection data. When the line fraction probed is low, only a small fraction of the particles are actually detected and the statistical variance of the measurement is high, rendering it less sensitive and useful for control and monitoring purposes. A high line fraction results in a high sensitivity measurement.

Typical prior art non-trapping detectors detect on order of about 1-5% of the one thousand particles based on a 1 cm beam diameter and 1 cm$^3$ volume from which scattered light can be collected and a total input port area of 100 cm$^2$ (10 cm×10 cm). In contrast, the line fraction probed in particle detectors that includes the trapping region according to the present invention is at least 10% and can be as high as 100% depending on the relative cross sectional areas of the charging region 212 (FIG. 2) and the input port 204. This high line fraction indicates that high sensitivity can be achieved with the particle detector of the present invention.

The statistical variance and the relative variance data show that it is important to count as many particles as possible in order to improve the variance. The data for the number of particles detected show that for high line fractions probed, particles entering the charging region 206 will travel to the detector location, which will result in a large enhancement in the effective area interrogated by the laser. For example, for a 95% line fraction probed and a one thousand particle environment, the improvement in relative variance is 9.5 times even without accounting for the ability to measure individual particles multiple times on sequential passes. Prior art non-trapping detectors cannot perform multiple measurements because particles passing through the detection system and the output port and are consequently lost to the system.

Figure 5A:
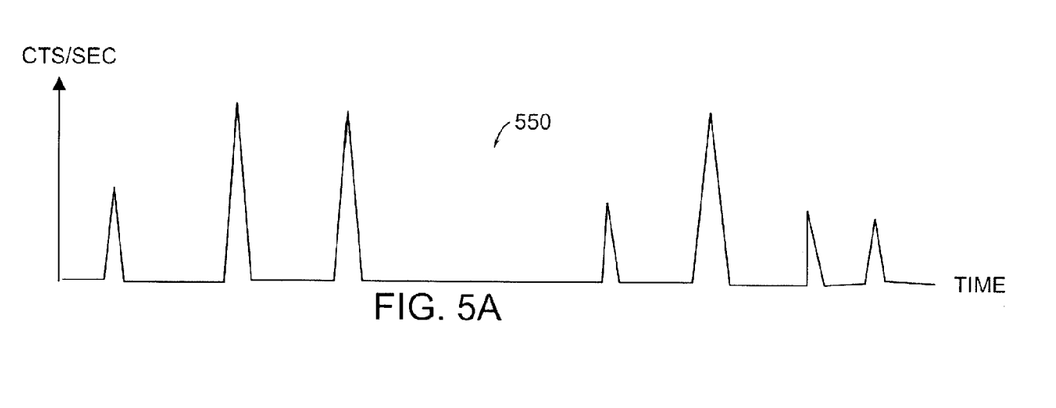
FIG. 5A illustrates a graph of the number of counts per second as a function of time for a particle detector according to the present invention where a relatively small number of particles are trapped in the trapping region.

FIG. 5A illustrates a graph 500 of the number of counts per second as a function of time for a particle detector according to the present invention where a relatively small number of particles are trapped in the trapping region. The graph 500 indicates that the light scattering events are not overlapping. The rate of particle detection indicates the population of particles in the trapping region 212 (FIG. 2). The power spectrum of the photodetector signal is a measure of the approximate size of the particles.

Figure 5B:
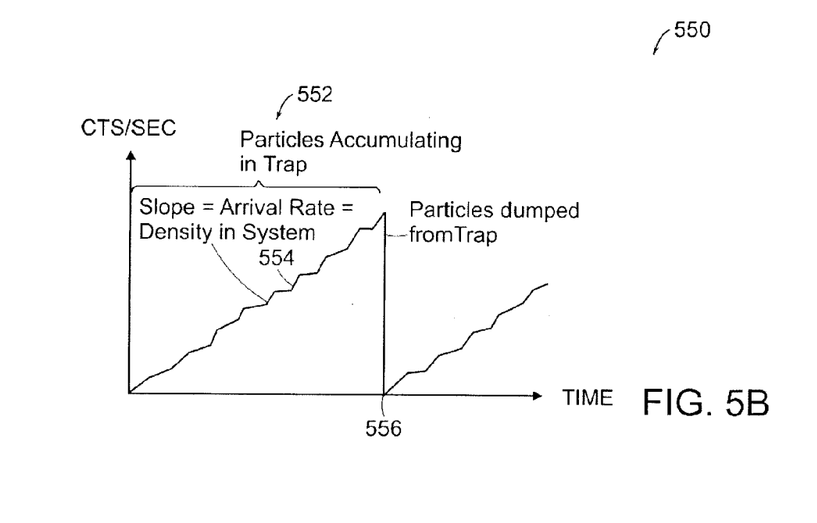
FIG. 5B illustrates a graph of the number of counts per second as a function of time for a particle detector according to the present invention with a trapping region that is periodically emptied.

FIG. 5B illustrates a graph 550 of the number of counts per second as a function of time for a particle detector according to the present invention with a trapping region that is periodically emptied. The particle detector is operated in a mode where the particles in the trapping region 212 (FIG. 2) are periodically "dumped" so that all particles exit, either to a physical trap, or to some exhaust port. The graph 550 shows an accumulation time period 552 where particles accumulate in the trap. Particles accumulate over time as particles enter the trap and the local number of particles increases. Detection can occur as scattered photons are generated when particles traverses the laser beam.

When the particle density is low, the particles are mostly detected as single detection events, and the signal as a function of time is as is shown in FIG. 5A. As the number of particles in the trap increases, the signal pulses become more frequent. As even more particles enter into the trap, the pulses overlap and eventually the signal 554 of FIG. 5B results where the signal is reflective of the total trap contents and is no longer reflective of an individual particle. The slope of the signal is proportional to the arrival rate.

The count rate is averaged over a period of time to determine a measure of the number of particles in the trapping region 212 (FIG. 2). The height of each pulse is a measure of particle size so that the particles in the trapping region 212 can be viewed as a histogram of sizes and numbers particles. Similarly, the power density of the measured photodetector signal can be used to derive the histogram of particle sizes. If many particles are present simultaneously in the system, a mode in which most or all of the photon pulses overlap will be reached. In this mode, the particles are simultaneously detected and the signal at the detector is a summation of multiple photodetector signals. The count per second signal has a positive slope as shown in FIG. 5A. The slope of the signal correlates to the rate of addition of photodetector signals or equivalently to the rate of arrival of particles at the input port 204. Because the signal may result from simultaneous scattering from many particles, it is possible to detect smaller particles for which the scattered photon signal from a single particle is below the detection limit.

Eventually, the number of particles in the trapping region 212 (FIG. 2) reaches a value where it is desirable to "dump" or remove the particles in the trapping region 212. At this time 556, the particles are expelled from the trapping region 212. The voltage potential in the charging region 206 can be manipulated to remove the potential well, which will free the particles from the trapping region 212.

Figure 6:
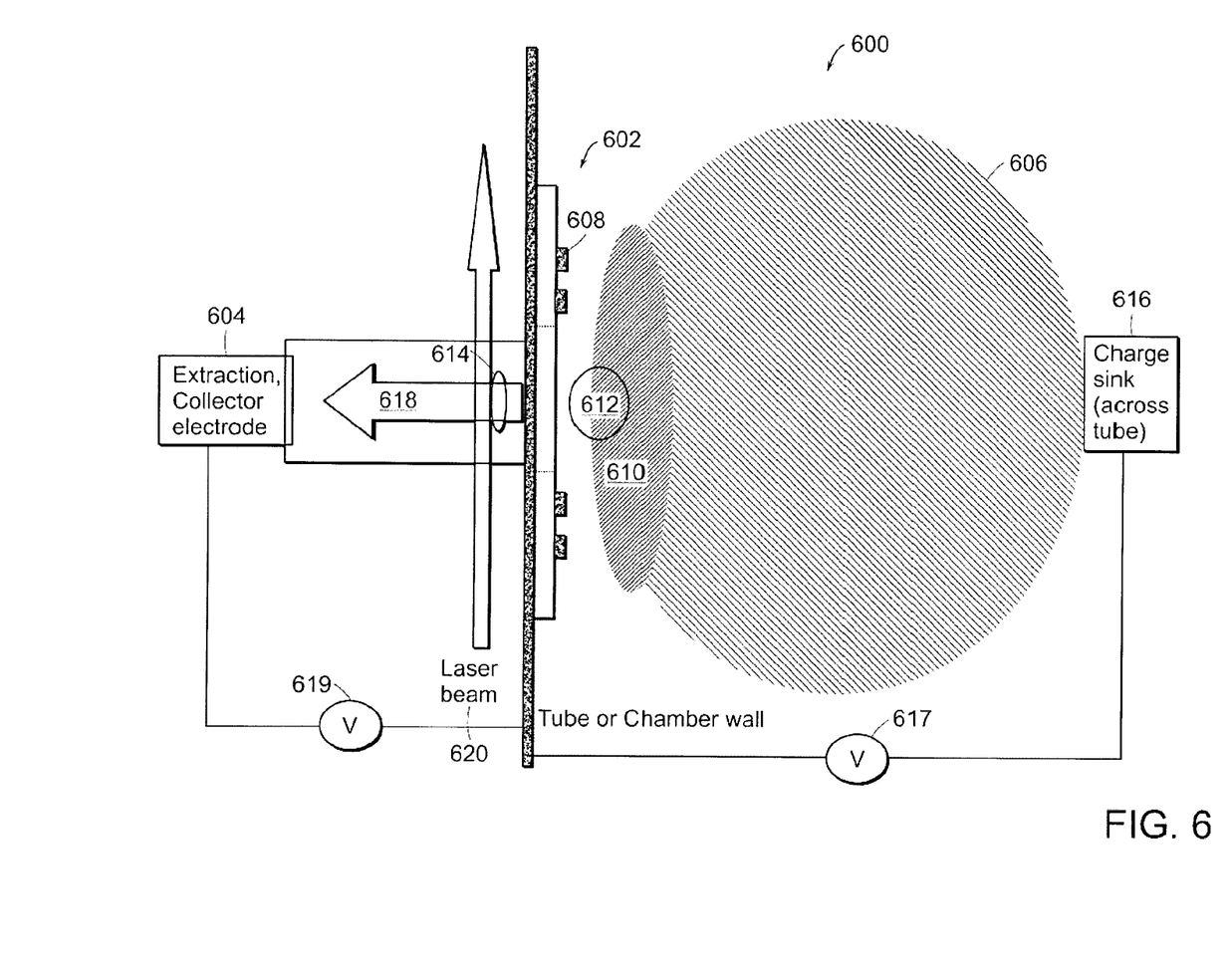
FIG. 6 illustrates an embodiment of a particle detector according to the present invention that includes a microplasma source and a particle extractor.

FIG. 6 illustrates an embodiment of a particle detector 600 according to the present invention that includes a microplasma source 602 and a particle extractor 604. In some embodiments, the particle detector 600 is in a tube, a chamber wall, or an instrument housing. The microplasma charging source 602 generates charged species in a charging region 606. Numerous other types of charging sources can be used with the particle detector of the present invention.

Microplasma charging sources generate relatively small volume microplasmas that are on order of a few cubic centimeters or less. Some microplasma sources inductively couple electric and magnetic fields with a high efficiency resonant antenna structure. See, for example, Hopwood, J. Vac. Sci. Technol. B, 18.5, Sep/October 2000, pg. 2446. Suitable microplasma sources are described in U.S. Pat. No. 7,123, 361, entitled "Microplasma Emission Spectrometer" and U.S. patent publication Ser. No. 10/907,024, entitled "Shielded Microplasma Source," which are incorporated herein by reference.

The microplasma charging source 602 shown in FIG. 6 includes a coil antenna 608 that generates a high density of charged species in a high density region 610 of the charging region 606. A trapping region 612 is formed in the high density region 610. The trapping region 612 is positioned adjacent to an output port 614. In some embodiments, the trapping region 612 has a volume and cross section that is substantially the same as the volume and the cross section of the output port 614. Charges are transported from the high density region 610 to the entire charging region 606. In some embodiments, a charge sink electrode 616 is positioned proximate to an edge of the charging region 606 and biased with a power supply 617 so as to attract charged species of opposite polarity.

The extractor electrode 604 is positioned adjacent to the trapping region 612 and the output port 614. The extractor electrode 604 is biased by a power supply 619 so that particles trapped in the trapping region 612 are expelled towards the extractor electrode 604. When the microplasma antenna 608, charge sink electrode 616, and the extractor electrode 604 are all properly biased, the particles in the trapping region 612 are extracted, thereby emptying or "dumping" the particles in the trapping region 612 through the output port 614 along the path 618.

For example, a positive bias applied to the extractor electrode 604 with power supply 619 and a negative bias applied to the charge sink electrode 616 with power supply 617 would generate forces on negatively charged particles which would move them towards the extractor electrode 604. Alternately, the operating conditions of the microplasma source 602 could be manipulated to cease plasma generation at which point the driving mechanism of trapping would be removed and the particles would exit, either in random directions or in a direction of an electric field that is generated by biasing an electrode or other surfaces of the particle detector.

A light source, such as a laser generates a light beam 620 that propagates across the output port 614 in a traverse direction relatively to the path 618 of the particles. Photons are generated from the interaction of the particles with the light beam 620. Particles traveling from the output port 614 can be detected with a detector as they scatter from the light beam 620. The particles traveling from the output port 614 can also be collected or analyzed once they reach the extractor electrode. Numerous types of particle collection and analysis systems, such as charge detection, time-of-flight measurement, and mass-to-charge ratio measurement and analysis systems can be used.

Such a particle detector has a relatively high probability of particle detection. The projected enhancement in particle detection probability over particle detectors that do not have trapping regions according to the present invention will increase as the ratio of the input port area to the trapping region area for the detector. This allows the use of detectors with smaller active areas, which is advantageous because such detectors typically have lower dark current noise.

EQUIVALENTS

While the present teachings are described in conjunction with various embodiments and examples, it is not intended that the present teachings be limited to such embodiments. On the contrary, the present teachings encompass various alternatives, modifications and equivalents, as will be appreciated by those of skill in the art, may be made therein without departing from the spirit and scope of the invention.

What is claimed is:

1. A particle detector comprising:
   a. an input port for receiving gas and particulate matter;
   b. a charging source that is coupled to the input port, the charging source generating positively and negatively charged species that charges at least some particulate matter in a charging region, thereby generating a plurality of charged particles;
   c. a trapping region positioned in the charging region, the trapping region having a potential well that attracts and confines the plurality of charged particles; and
   d. a detector that detects charged particles in the trapping region.

2. The particle detector of claim 1 wherein a cross sectional area formed at a boundary of the input port and the charging region is much larger than a cross sectional area of the trapping region.

3. The particle detector of claim 1 wherein a volume of the charging region is much larger than a volume of the trapping region.

4. The particle detector of claim 1 further comprising an output port for passing the plurality of charged particles out of the trapping region.

5. The particle detector of claim 4 wherein a cross sectional area of the output port is substantially the same as a cross sectional area of the input port.

6. The particle detector of claim 4 wherein a cross sectional area of the output port is substantially the same as a cross sectional area of the trapping region.

7. The particle detector of claim 1 wherein the charging source comprises a microplasma source, the trapping region being formed from a localized high plasma density generated by the microplasma source that generates the potential well in the charging region.

8. The particle detector of claim 1 further comprising a hollow-cathode structure that generates a localized region of relatively high particle density plasmas which generates the potential well in the trapping region.

9. The particle detector of claim 8 wherein the hollow-cathode structure comprises a driving electrode that generates the positively and negatively charged species.

10. The particle detector of claim 1 further comprising at least one electrode that is positioned proximate to the charging region, the at least one electrode being electrically biased so as to create a potential energy gradient across the charging region that forms the potential well in the trapping region.

11. The particle detector of claim 1 wherein drag forces assist in forming the potential well that attracts and confines the plurality of charged particles.

12. The particle detector of claim 1 wherein gravitational forces assist in forming the potential well that attracts and confines the plurality of charged particles.

13. The particle detector of claim 1 wherein the detector comprises an electrical detection system.

14. The particle detector of claim 1 wherein the detector comprises a light scattering detection system that uses an interrogation light beam to detects at least some of the plurality of charged particles in the trapping region.

15. The particle detector of claim 14 wherein a beam width of the interrogating light beam is approximately equal to a width of the trapping region.

16. The particle detector of claim 14 wherein a beam width of the interrogating light beam is approximately equal to a width of an output port that passes the plurality of charged particles out of the trapping region.

17. The particle detector of claim 1 further comprising a light scattering detection system that uses an interrogation light beam to detect at least some of the plurality of charged particles as they exit the trapping region.

18. The particle detector of claim 1 wherein at least part of the detector that detects charged particles is positioned in the charging region.

19. The particle detector of claim 1 further comprising at least one electrode positioned opposite the charging region, the at least one electrode generating an electric potential that attracts at least some of the plurality of charged particles through an output port.

20. A method of detecting particles, the method comprising:
   a. receiving gas phase matter containing particles;
   b. generating positively and negatively charged species in a charging region, the positively and negatively charged species generating a plurality of charged particles;
   c. creating a potential energy gradient and minimum in the charging region that attracts and confines the plurality of charged particles in a trapping region; and
   d. detecting the plurality of charged particles confined in the potential energy minimum.

21. The method of claim 20 wherein the detecting the plurality of charged particles in the trapping region comprises detecting the plurality of charged particles after they exit the trapping region.

22. The method of claim 20 wherein the detecting the plurality of charged particles comprises detecting the plurality of charged particles with an electrical detection system.

23. The method of claim 20 wherein the detecting the plurality of charged particles comprises detecting the plurality of charged particles with a light scattering detection system.

24. The method of claim 20 further comprising generating an electric field that attracts at least some of the plurality of charged particles out of the trapping region.

25. The method of claim 20 further comprising manipulating an electric field present in the trapping region to extract at least some of the plurality of charged particles out of the trapping region.

26. The method of claim 20 further comprising analyzing the detected plurality of charged particles.

27. The method of claim 20 wherein the detecting at least some of the plurality of charged particles comprises simultaneously detecting multiple charged particles.

28. The method of claim 20 further comprising periodically removing the charged particles from the trapping region.

29. The method of claim 20 wherein the creating the potential energy gradient and minimum in the charging region comprises generating a microplasma.

30. The method of claim 20 wherein the creating the potential energy gradient and minimum in the charging region comprises generating a relatively high particle density plasmas with a hollow-cathode structure.

31. The method of claim 20 wherein the creating the potential energy gradient and minimum in the charging region comprises generating an electric field with an electrode.

32. The method of claim 20 wherein the creating the potential energy gradient and minimum in the charging region comprises applying at least one of gravitational and drag forces to the particles.

33. A particle detector comprising:
a. means for receiving gas phase matter containing particles;
b. means for generating positively and negatively charged species in a charging region, the positively and negatively charged species generating a plurality of charged particles;
c. means for creating a potential energy gradient and minimum in the charging region that attracts and confines the plurality of charged particles; and
d. means for detecting the plurality of charged particles.

* * * * *